United States Patent
Christensen et al.

Patent Number: 5,942,408
Date of Patent: Aug. 24, 1999

[54] PROCESS CHALLENGE DEVICE AND METHOD

[76] Inventors: Dennis E. Christensen, 23575 Cabot Blvd., #1205, Hayward, Calif. 94545; R. Daniel Webster, 1409 Mallard Way, Sunnyvale, Calif. 94087; Harvey A. Markinson, 147 Bannister Way, Alameda, Calif. 94502

[21] Appl. No.: 08/887,753

[22] Filed: Jul. 3, 1997

Related U.S. Application Data

[60] Provisional application No. 60/022,393, Jul. 29, 1996.

[51] Int. Cl.⁶ .................................................. C12Q 1/22
[52] U.S. Cl. .................... 435/31; 435/287.4; 435/805; 422/1; 422/26; 422/28; 422/58
[58] Field of Search ............................. 435/287.1, 287.4, 435/287.7, 287.8, 805, 31; 422/56, 58, 1, 26, 28, 32

[56] References Cited

U.S. PATENT DOCUMENTS

| | | | |
|---|---|---|---|
| 2,998,306 | 8/1961 | Huyck et al. | 435/287.4 |
| 3,711,378 | 1/1973 | Kereluk | 435/287.4 |
| 4,121,714 | 10/1978 | Daly et al. | 206/363 |
| 4,211,323 | 7/1980 | Olsen | 206/210 |
| 4,358,015 | 11/1982 | Hirsch | 206/439 |
| 4,602,910 | 7/1986 | Larkin | 604/87 |
| 4,608,043 | 8/1986 | Larkin | 604/87 |
| 4,839,291 | 6/1989 | Welsh et al. | 435/296 |
| 4,910,147 | 3/1990 | Bacehowski et al. | 435/296 |
| 5,132,211 | 7/1992 | Lundin et al. | 435/31 |
| 5,759,848 | 6/1998 | Nagoshi et al. | 435/287.1 |

Primary Examiner—David A. Redding
Attorney, Agent, or Firm—Gregory S. Smith; James J. Leary; Carol D. Titus

[57] ABSTRACT

A process challenge device tailored to mimic the resistance of a particular product to a particular biological inactivation, disinfection, or sterilization process, and used to challenge the process, thus providing a means to validate the efficacy of the process. The process challenge device is used by subjecting the device containing indicator organisms to an inactivation or sterilization process, and culturing any surviving indicator organisms as a means to assess the efficacy of procedures for the inactivation of microorganisms. The device includes a biological indicator organism stored on a carrier substrate enclosed within a chamber formed by a barrier film material. The specific indicator organism and carrier substrate are chosen for their appropriateness for a given process. The materials comprising the barrier film material of the process challenge device are chosen for the materials' specific resistance to the given process. The process challenge device may also comprise a separate second chamber filled with an appropriate culture medium that is separated from the chamber containing the biological indicator by a separation means, such as a valve, a clip, or a frangible separation. The separation means between the two chambers is capable of being removed on demand after completion of the process thus allowing the culture medium to contact the biological indicator. This initiates the beginning of the culture phase which confirms non-survivability of the organism population and thus process efficacy. The incorporation of the culture medium into the device permits a level of convenience to the user not available in prior art inventions.

22 Claims, 2 Drawing Sheets

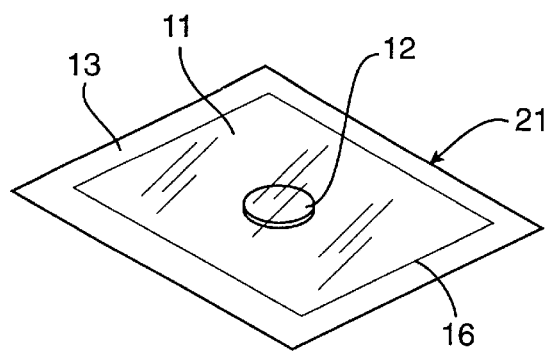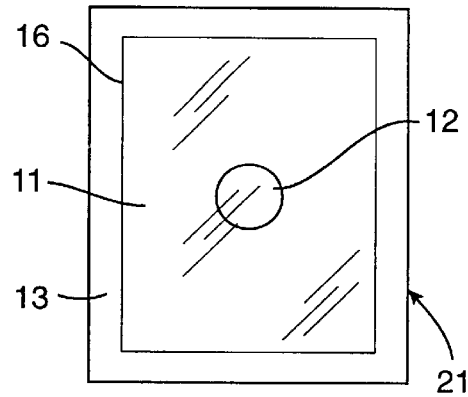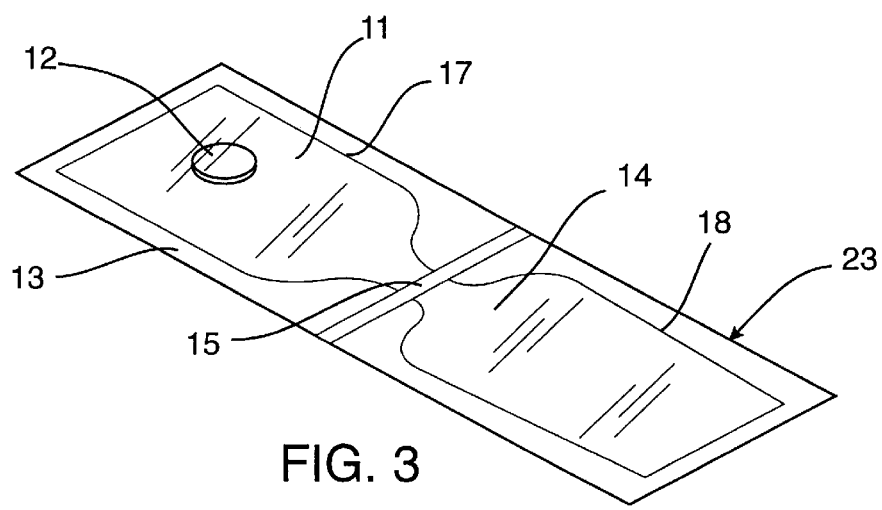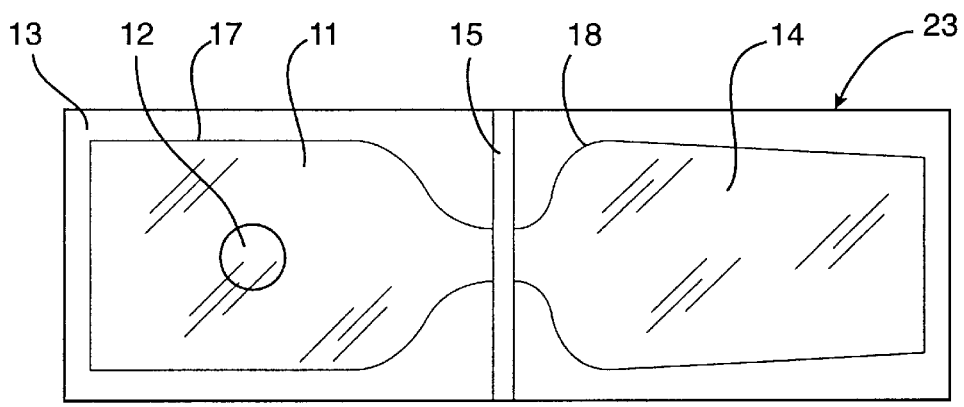

PROCESS CHALLENGE DEVICE AND METHOD

CROSS REFERENCE TO RELATED APPLICATIONS

This application claims the benefit of the provisional patent application of Dennis Christensen, R. Daniel Webster, and Harvey Markinson, for a Process Challenge Device, Ser. No. 60/022,393 filed on Jul. 29, 1996, which application is hereby incorporated by reference in its entirety.

BACKGROUND OF THE INVENTION

1. Field of the Invention

This invention relates generally to process challenge devices, in particular to process challenge devices, using biological indicator organisms sealed in containers made from specially chosen materials, used to assess the efficacy of procedures for the inactivation of microorganisms in industries related to health care, food packaging and preparation, and other industries that use biological indicators.

2. Description of the Prior Art

Presently, there are two conventional methods to test the effectiveness of a given sterilization, disinfection, or biological inactivation process (hereafter referred to collectively as "inactivation process"). The first is to inoculate a sample product with a known quantity of a specific indicator organism (the "inoculate"), subject the inoculated product to the appropriate process, recover the sample inoculate, and culture the inoculate in a specific growth medium to determine whether there were any surviving organisms. The second is to use a biological indicator which is inoculated with a known quantity of a specific indicator organism, subject the biological indicator to the appropriate process, and culture the biological indicator to determine whether there are any surviving organisms. Typically, in both cases the absence of growth of the indicator organisms in the growth medium indicates a successful inactivation process. Direct inoculation of sample product is generally done during early validation of a biological inactivation process. Biological indicators are generally used to test repeat processing.

Currently there are three primary inactivation processes employed in the health care industry: steam, ethylene oxide gas, and ionizing radiation. Several other processes such as dry heat, hydrogen peroxide, chlorine dioxide, peracetic acid, ozone, and plasma are also in various stages of use and acceptance.

Each of these inactivation processes require unique biological indicator organisms, growth media, and procedures to confirm sterilization effectiveness. Among the problems associated with confirming biological inactivation and thus the effectiveness of process are: (a) the lack of commercial availability of appropriate carrier media for some of the newer processes; (b) the difficulty in inoculating products to be tested due to product/package configuration; (c) the cost of using actual products that must be sacrificed for the initial process qualification and the lot-to-lot verification of the process in every process test cycle; and (d) concerns regarding worker exposure to certain of the chemical sterilants, (for example, the European Standard for ethylene oxide processing requires removal of the biological samples prior to degassing the product).

Self-contained process challenge devices containing biological indicator organisms which do not require inoculation of a product are in use in health care facilities such as hospitals. The resistance of a process challenge device to a particular biological inactivation process is given as a D Value which is defined as the exposure time required under a defined set of conditions to cause a 1-logorithm or 90% reduction in the population of a particular organism. Process challenge devices currently on the market have a single unchanging D Value. In order to create the higher resistance to the inactivation process experienced by actual product being processed, due to packaging of the product, the location of a product within a load being processed, or other factors, these devices must generally be wrapped or contained within packaging or other protective material similar to that used on the products being sterilized, so that the process challenge device is exposed to the same environment as the products being processed. Alternativley, in some cases the process challenge device is buried in the most protected location within a load being sterilized. Therefore, these devices cannot be used alone to validate a biological inactivation process without additional protection from the process to simulate the higher resistance of the actual products to the process.

For example, Welsh et al., U.S. Pat. No. 4,839,291, discloses a process challenge device which is composed of a number of elements including an outer tube and an inner tube assembled in a manner intended to create a tortuous path to impede the flow of sterilant to the biological indicator contained within the tubes, thereby creating a D Value. Typical of many prior art devices, the device of Welsh et al. is larger and more expensive to manufacture than the present invention, and its resistance to a particular sterilization process may not be easily and accurately varied merely by using slightly different materials in construction of the device. Additionally, the materials used may not be suitable for the newer inactivation processes, such as hydrogen peroxide, ozone, and plasma, because the sterilants used may destructively react with elements of the process challenge device.

It would be a significant advantage to provide a process challenge device which overcomes the disadvantages of the prior art devices, and which can, in addition, be constructed with resistance tailored to a particular biological inactivation process to avoid the need for destructive testing of product, the need for additional packaging of or protective covering over the process challenge device, or the necessity of placing one or more devices within an actual load.

SUMMARY OF THE INVENTION

It is an object of the present invention to provide a convenient, low cost device to challenge biological inactivation process effectiveness.

It is a further object of the present invention to provide a process challenge device which may be easily constructed with variable resistance to a particular biological inactivation process by substitution of known materials having known resistances to the particular process.

It is an additional object of the present invention to provide a process challenge device which can be constructed with a resistance to a particular biological inactivation process at least as great as the resistance of the product typically processed, so that the process challenge device may be used alone to test the inactivation process, without accompanying materials or products.

Another object of the present invention is to provide a package system containing a biological indicator and, optionally, an integral growth medium that is specific to any given biological inactivation process.

It is a further object of the present invention to provide a process challenge device which can be safely, conveniently, and easily recovered for subsequent culturing to confirm and assure process effectiveness.

These and other objects of the present invention are achieved in a process challenge device that includes a single or multi-chamber sealed pouch or the like that contains at least one biological indicator and may also contain a cell culture medium. The pouch is composed of one or more layers of a web or film material (hereafter referred to as "film material"). Different portions of the device may be formed of different materials.

Domestic and international regulatory guidelines permit the use of biological process challenge devices that demonstrably have resistance to sterilization equal to or greater than the material or product and package combination to be subjected to the process, which process is being tested by the process challenge device. The "product package combination" refers to the characteristics of the product itself and of any associated packaging which may exist as these characteristics relate to or effect the product and package combinations resistance to a particular inactivation process. A product and package combination including no packaging is included in this definition.

The pouch of the present invention is fabricated from a suitable single or multiple film layer or multi-layer film laminate that is chosen to offer the appropriate level of resistance to the inactivation process. The magnitude of resistance to the inactivation process is determined by knowledge of the product and packaging configuration and characteristics, the biological inactivation method of choice, and the appropriate laboratory studies which can confirm the equivalency of biological inactivation of the device to the specific product and package combination. The resistance of the film material is typically measured by gas permeation, and temperature and chemical resistance values which are well known in the industry.

By knowing the specific characteristics of the biological inactivation process to be tested, the film material or materials to be used in construction of the process challenge device may be chosen based on the known gas permeation, temperature and chemical resistance values of available film materials. This results in a process challenge device which can be used alone to mimic the resistance to the inactivation process experienced by the product being processed, rather than requiring that the process challenge device be processed with a load, or with additional packaging or protections to simulate product resistance to the process.

The biological indicator is typically commercially available on a small cellulose disk or strip carrier or substrate inoculated with a known population of a known organism. However, it is comprehended that other carrier media may be used with the present invention. Such other carrier media may include metals, fiber glass, microporous polymeric compounds including polypropylene, polyethylene, and polysulfone, and ceramics.

In some preferred embodiments, the process challenge device of the present invention may include process exposure indicators. Any means for visually indicating that the device has been exposed to the inactivation process may be used, however, a paper label which is chemically treated to change color when the device has been exposed to the biological inactivation process is preferable.

The process challenge device may also contain a separate additional chamber filled with a culture medium tailored for the specific indicator organism which will be used. The second chamber is separated from the chamber containing the biological indicator by a separation means, such as a valve, a clip, heat seal, or a frangible separation. The separation means between the two chambers is capable of being opened, ruptured, or removed on demand after completion of the inactivation process thus allowing the culture medium to contact the biological indicator organisms. This initiates the beginning of the culture phase which confirms non-survivability of the organism population and thus process efficacy. The incorporation of the culture medium into the device permits a level of convenience to the user not available in prior art inventions.

BRIEF DESCRIPTION OF THE DRAWINGS

FIG. 1 is a perspective view of a first embodiment of the process challenge device of the present invention.

FIG. 2 is a plan view of the process challenge device of FIG. 1.

FIG. 3 is a perspective view of a second embodiment of the process challenge device having an integral culture medium chamber.

FIG. 4 is a plan view of the process challenge device of FIG. 3.

DETAILED DESCRIPTION OF THE INVENTION

Figure 5:
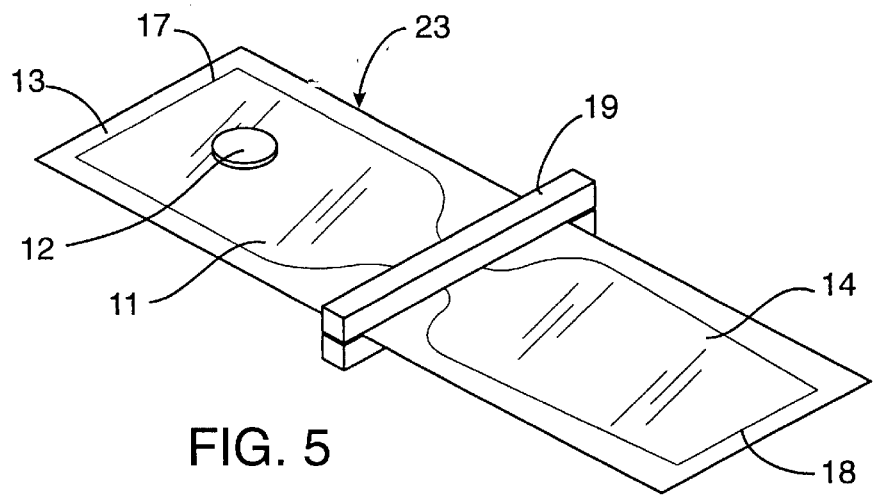
FIG. 5 is a plan view of the second embodiment of the process challenge device of FIG. 4 having a clip separating the biological indicator chamber from the culture chamber.

Biological inactivation process validation and verification of process effectiveness are important aspects of any inactivation process for medical devices or pharmaceuticals or any treatment process for sterilization, biological inactivation or disinfection of food products.

Presently, the conventional way to test the effectiveness of a given inactivation process is to inoculate sample product with a known quantity of a specific indicator organism (the "inoculate"), subject the inoculated product to the appropriate process, recover the sample inoculate, and culture the inoculate in an appropriate growth medium to determine whether there were any surviving indicator organisms.

The international guidelines for sterilization of health care products allows for the use of a "process challenge device" as an alternative to the conventional method of process validation and biological inactivation verification described above. In this method, a process challenge device is cycled through the process with the products and then separately analyzed to determine the efficacy of the process. The process challenge device must be as resistant or more resistant, to the inactivation process than the product and package combination being sterilized. Normally this requires that the process challenge device be protected within actual product being processed, or otherwise protected in order to mimic the resistance of the product to the process. The prior art has the additional disadvantages discussed previously.

The present invention provides a process challenge which overcomes the disadvantages of the prior art devices. A first preferred embodiment of the process challenge device of the present invention, generally referenced by the number 21, is shown in a perspective view in FIG. 1 and in a plan view in FIG. 2. In this preferred embodiment, the process challenge device has a chamber 16 which is enclosed by a barrier film material 11. In a preferred embodiment, the chamber 16 of the process challenge device may be formed by sealing two separate pieces of barrier film material 11 together to form a front and a back panel or a single continuous piece of barrier film material 11 may be folded and sealed to form chamber 16. Where two pieces of barrier film material 11 are used, the front and back panels may be made of the same or different material. The barrier film material 11 is sealed by a peripheral seal 13 around the edges of the chamber 16. Within the chamber 16 is a biological indicator 12. Biological indicator 12, in one preferred embodiment, is a cellulose disk inoculated with a known quantity of a biological indicator organism which may be one of several types chosen for the organism's appropriateness to the method of biological inactivation to be used. For ethylene oxide gas sterilization, the recommended biological indicator 12 has a $10^6$ (microorganisms per indicator) concentration of *Bacillus subtilis*, typically on a cellulose substrate. The international guidelines for steam sterilization recommend a biological indicator 12 with a $10^6$ concentration of *Bacillus stearothermophilus*. For food processing a biological indicator 12 inoculated with Clostridium is preferred. Other preferred microorganisms include *Bacillus circulans, Bacillus cereus*, and *Bacillus Pumilus*.

Other newer types of inactivation processes, such as hydrogen peroxide, ozone, plasma, or chlorine dioxide may be reactive with the cellulose substrate of biological indicator 12. Therefore, for these processes, a substrate other than cellulose should be used for biological indicator 12, such as a fibrous polyester substrate, a porous ceramic, fiber glass, or a substrate composed of plastics such as microporous polymeric compounds including polypropylene, polyethylene, or polysulfone, or a nonporous inorganic substrate such as a metal, glass or fiberglass.

Barrier film material 11 of the process challenge device is designed to create a specific resistance greater than or equal to that of the material or product package combination being treated by a specific process, and any related packaging associated with the material. The process resistance of the challenge device is determined by the properties of the barrier film material or materials chosen. Such properties include gas permeability, radiation transmission, and temperature and chemical resistance. Suitable candidate materials for barrier film material 11 include, but are not limited to, polymer film materials, such as polyolefins (e.g. polyethylene or polypropylene), polyesters (e.g. polyethylene terephthalate (mylar®)), polybutylene terephthalate, or PETG copolyester, polyamides (nylons), vinyl-chloride polymers, polyvinylidene chloride (e.g. SARAN®), polyvinylidene flouride, polyamides, ethylene-vinyl acetate, ethylene vinyl alcohol, aluminized polyester, etc., or nonpolymer films, such as aluminum foil, silica oxide and alumina oxide, either separately or in combination. Multilayer films which are laminated with adhesive or formed by coextrusion may also be used. If desired, barrier film material 11 may also include vent materials, such as spun bonded polyolefin (e.g. Tyvek® or the like) or expanded polytetrafluoroethylene (e.g. Goretex® or the like). Barrier film material 11 may constitute an inner barrier film material enclosed within an outer barrier film material to simulate the sterilization resistance of double-pouch packaging which is currently prevalent for packaging surgical devices and interventional products.

Biological indicator 12 is placed within chamber 16, which chamber is then sealed by a peripheral seal 13 around the edges of barrier film material 11. The method of making the peripheral seal 13 around the edges of barrier film material 11 is chosen (a) for compatibility with the material or materials of barrier film material 11, and (b) to provide an appropriate level of process resistance. Methods for making peripheral seal 13 include but are not limited to heat sealing, including isothermal, impulse and radio frequency heating, ultrasonic sealing and adhesive sealing. The interior of chamber 16 within barrier film material 11 may be filled with a selected atmosphere, such as sterile air, filtered air, or an inert gas, before it is sealed. Alternatively, barrier film material 11 may be vacuum sealed after the biological indicator 12 is placed within chamber 16.

In a preferred embodiment, the exterior appearance of the process challenge device may be in the format of a flexible heat-sealed pouch, as illustrated in FIGS. 1 and 2. However, in alternative preferred embodiments, the process challenge device may be made in other formats such as a heat-sealed thermoformed tray or a form-fill-and-seal pouch or tray. The choice of the format and the manufacturing process for the process challenge device will depend on, among other things, the material or materials selected for barrier film material 11, the nature of the product and packaging combination, and the particular process in which the process challenge device will be used, and the economics of the process challenge device manufacturing process.

In some preferred embodiments, the process challenge device 21 of the present invention may include process exposure indicators. Any means appropriate for visually indicating that the device has been exposed to the inactivation process may be used, and a large number of such indicators are commercially available.

In use, for either process validation or verification, a process challenge device 21 constructed with materials chosen to mimic the resistance of product exposed to the inactivation process is used. Alternatively, one or more process challenge devices 21 are placed at various locations within a load or processing batch, preferably on the exterior of the product packaging at different locations within the load. Time is saved by not having to inoculate sample products before they are packaged and no actual packaged products have to be sacrificed. The load is then subjected to the chosen sterilization or inactivation cycle or other applicable process. After the process cycle, the process challenge devices 21 are removed and taken to a laboratory where biological indicator 12 is removed from chamber 16 and incubated in an appropriate culture medium for culturing. The absence of growth of indicator organisms indicates a successful sterilization, biological inactivation process, or disinfection process. Further time is saved and personnel exposure to any residual sterilizing agent in the sterilized products is reduced because the packages do not have to be opened for retrieval of the process challenge devices. This is an important advantage of the invention over the prior art for ethylene oxide gas sterilization because ethylene oxide gas is a suspected carcinogen and under current regulations employee exposure to the residual gas must be limited to 0.5 PPM/8 hours.

A second preferred embodiment of the process challenge device of the present invention, generally referenced by the number 23, is shown in a perspective view in FIG. 3 and in a plan view in FIG. 4. In this second preferred embodiment, the process challenge device has a first chamber 17 and a second chamber 18 enclosed within a barrier film material 11. The process challenge device may be formed by sealing two separate pieces of barrier film material 11, formed of either the same or different material, together to form a front and a back panel or by folding and sealing a single continuous piece of barrier film material 11. In alternate embodiments, a different barrier film material may be used for each chamber. The barrier film material 11 is sealed by a peripheral seal 13 around the exterior edges of the first chamber 17 and the second chamber 18. The first chamber 17 and the second chamber 18 are physically separated by a breachable separation means such as a frangible seal 15. Alternative separation means may include clips or valves or other known separation means, preferred embodiments of which can be seen in FIGS. 5 and 6. Within the first chamber 17 is a biological indicator 12 in substantially the same form as previously discussed. Second chamber 18 is filled with an appropriate culture medium 14, which may be one of several types, chosen for its appropriateness to the indicator organism used for biological indicator 12 and the method of biological inactivation to be used. A liquid culture medium such as a soybean casine digest medium or the like is preferred for culture medium 14. In alternative embodiments, a gelatin medium could be used.

Other newer types of inactivation processes, such as hydrogen peroxide or ozone plasma may be reactive with the cellulose substrate of biological indicator 12. Therefore, for these processes, a substrate other than cellulose should be used for biological indicator 12, such as a fibrous polyester substrate, a porous ceramic, fiber glass, or a substrate composed of plastics such as microporous polymeric compounds including polypropylene, polyethylene, and polysulfone, or a nonporous inorganic substrate such as a metal, glass or fiberglass. For example, in a currently preferred embodiment for hydrogen peroxide sterilization treatment, the biological indicator 12 has a $10^6$ concentration of *Bacillus stearothermophilus* on a non-reactive substrate of microporous filter medium, preferably of a non-reactive polymer such as polypropylene, polyethylene or polysulfone. In alternate embodiments, other desirable microorganisms may be used.

The barrier film material 11 surrounding the first chamber 17, which contains biological indicator 12, is chosen to be as resistant or more resistant to the inactivation process than the product/package combination to be treated. Barrier film material 11 surrounding second chamber 18, which contains culture medium 14, may be identical to barrier film material 11 of first chamber 17, or a different barrier material may be chosen. Depending on the culture medium 14 and the inactivation process chosen, a more resistant barrier material may be preferred for second chamber 18 in order to protect culture medium 14 from the biological inactivation process. If for example, the chosen culture medium 14 is reactive to the sterilizing agent used in gas sterilization, a gas impermeable barrier material may be used for barrier film material 11 of second chamber 18. Similarly, if the chosen culture medium 14 is susceptible to radiation degradation, then a barrier material that is more opaque to the wavelength or the particle energy used for radiation sterilization may be used for barrier film material 11 of second chamber 18. Alternatively, in some circumstances it may be desirable to use a less resistant barrier material for barrier film material 11 of second chamber 18 if it is desired to assure the sterility of culture medium 14 simultaneously with sterilizing the materials to be treated.

Suitable candidate materials for barrier film material 11 of first chamber 17 and second chamber 18 include, but are not limited to, those film materials previously discussed including single and multiple layers of barrier film material and multi-layer laminate barrier film materials. Peripheral seal 13 around the edges of barrier film material 11 may be made by heat sealing, including isothermal, impulse and radio frequency heating, ultrasonic sealing or by adhesive sealing. If desired the interior of first chamber 17 and/or second chamber 18 may be filled with a selected atmosphere prior to sealing.

In some preferred embodiments, the process challenge device 23 of the present invention may include process exposure indicators. Any means for visually indicating that the device has been exposed to the inactivation process may be used, however, a paper label which is chemically treated to change color when the device has been exposed to the biological inactivation process is preferable.

In one preferred embodiment, seen in FIGS. 3 and 4, the frangible seal 15 which separates first chamber 17 and second chamber 18 may also be made by heat sealing, including isothermal, impulse and radio frequency heating, ultrasonic sealing or adhesive sealing. However, frangible seal 15 should be made more susceptible to rupture than peripheral seal 13. This may be done by using a weaker adhesive, or a lower heat sealing temperature for sealing frangible seal 15. Preferably, the geometry of frangible seal 15 may also be used to enhance the ease of rupturing frangible seal 15 relative to peripheral seal 13. For example, frangible seal 15 may have a seal width which is narrower than that of peripheral seal 13. Alternatively, a stress riser, like the chevron shaped seal or a narrow passage 22, as shown in FIGS. 3, 4, and 7, connecting first chamber 17 and second chamber 18, interrupted by the frangible seal 15, may be used to concentrate the pressure, making the frangible seal 15 more easily ruptured.

Figure 6:
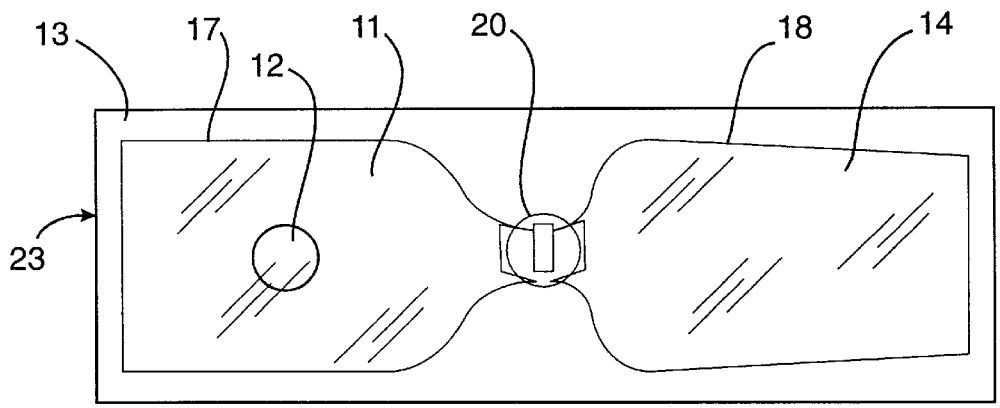
FIG. 6 is a plan view of the second embodiment of the process challenge device of FIG. 4 having a valve separating the biological indicator chamber from the culture chamber.

In alternative embodiments, a clip 19, best seen in FIG. 5, may be used to separate first chamber 17 and the second chamber 18. In use, after the process challenge device 23 has been subjected to the appropriate process, the clip is simply removed and the culture medium 14 caused to contact the biological indicator 12. Any clip which will effectively prevent culture medium 14 from entering first chamber 17 until the clip is removed may be used. In other embodiments, a valve 20, best seen in FIG. 6, may be used to separate the first chamber 17 and the second chamber 18. In use, after the process challenge device 23 has been subjected to the appropriate process, the valve is opened and the culture medium 14 is then caused to contact the biological indicator 12. Any valve which will effectively prevent culture medium 14 from entering first chamber 17 until the valve is opened may be used.

Figure 7:
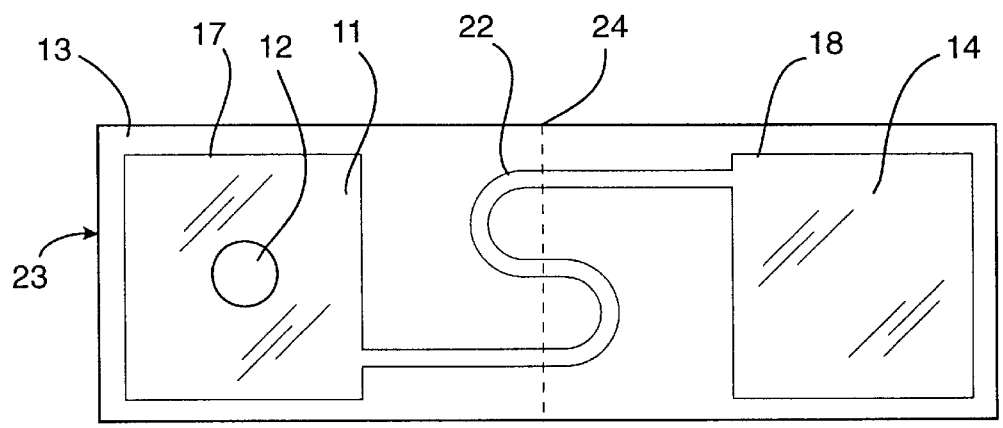
FIG. 7 is a plan view of the third embodiment of the process challenge device of FIG. 4 having a tortuous path separating the biological indicator chamber from the culture chamber.

In a third preferred embodiment, best seen in FIG. 7, a tortuous path 22 is used to separate first chamber 17 from second chamber 18. Resistance to the passage of medium 14 from second chamber 18 to first chamber 17 can be adjusted by varying the geometry of the channel of tortuous path 22. Reference number 24 points to a dotted line which is intended to indicate a fold line. Folding the process challenge device 23 along fold line 24 provides an additional barrier to the passage of medium 14 from second chamber 18 to first chamber 17. In alternate embodiments, just tortuous path 22 or just fold line 24 could be used to prevent passage of medium 14 from one chamber to the other, rather than both tortuous path 22 and fold line 24.

In use, for either process validation or verification, a process challenge device 23 constructed with materials chosen to mimic the resistance of product exposed to the inactivation process is used. Alternatively one or more process challenge devices 23 are placed at various locations within a load or processing batch, preferably on the exterior of the product packaging at different locations within the load. The load is then subjected to the chosen biological inactivation cycle or other applicable process. After the process cycle, the process challenge devices 23 are removed from the load and the separation means between first chamber 17 and second chamber 18 is broken or removed, allowing transfer of the culture medium 14 to the first chamber 17 containing the biological indicator 12. There is no need to transfer the process challenge device to a laboratory, as everything needed for culturing the indicator organism is contained within the process challenge device. Only an incubator or other controlled temperature chamber is needed to incubate the biological indicator 12 in the culture medium 14. The absence of growth of the indicator organisms indicates a successful sterilization, biological inactivation process or disinfection process.

Additional savings are realized with this second preferred embodiment of the process challenge device because further time and expense are saved in not having to prepare culture medium or culture tubes in which to incubate the indicator organisms, thereby avoiding the need for a complete laboratory. By eliminating many of the laboratory procedures, it also reduces the level of training needed for most of the process steps of inactivation process validation or sterility verification, thereby reducing the likelihood of errors. It also reduces personnel exposure to the indicator organisms and the culture medium and to any residual sterilizing agent that may be present in the biological indicator.

The preferred embodiments described herein are illustrative only and although the examples given include many specificities, they are intended as illustrative of several possible embodiments of the invention. Other embodiments and modifications will, no doubt, occur to those skilled in the art. Thus, the examples given should only be interpreted as illustrations of some of the preferred embodiments of the invention, and the full scope of the invention should be determined by the appended claims and their legal equivalents.

What is claimed is:

1. A process challenge device comprising:
a chamber formed by a first barrier film; and
a biological indicator stored on a carrier substrate, said carrier substrate enclosed within said chamber formed by said first barrier film;
wherein the combination of said biological indicator, said carrier substrate, and said first barrier film are tailored for use in a particular sterilization, biological inactivation, or disinfection process used on a particular product and package combination,
and wherein said barrier film material is comprised of a material selected from the group consisting of:
polyolefins,
polyesters,
polybutylene terephthalate,
PETG copolyester,
vinyl-chloride polymers,
polyvinylidene chloride,
polyvinylidene flouride,
polyamides,
ethylene vinyl alcohol,
ethylene vinyl acetate,
aluminized polyester,
silica oxide, and
alumina oxide.

2. The process challenge device of claim 1 wherein said first barrier film provides a resistance to a particular sterilization, biological inactivation, or disinfection process greater than or equal to a particular product and package and combination.

3. The process challenge device of claim 1 wherein said carrier substrate is comprised of a material selected from the group consisting of:
cellulose,
polyester,
ceramic,
plastic,
glass,
fiberglass, and
metal.

4. The process challenge device of claim 1 wherein said chamber further comprises a front film and a back film, said front film being formed from a material with properties different than a material forming said back film.

5. A process challenge device comprising:
a chamber formed by a first barrier film; and
a biological indicator stored on a carrier substrate, said carrier substrate enclosed within said chamber formed by said first barrier film;
wherein the combination of said biological indicator, said carrier substrate, and said first barrier film are tailored for use in a particular sterilization, biological inactivation, or disinfection process used on a particular product and package combination,
and wherein said biological indicator is an organism selected from the group consisting of:
*Bacillus subtilis,*
*Bacillus stearothermophilus,*
*Clostridium,*
*Bacillus circulans,*
*Bacillus cereus,* and
*Bacillus Pumilus.*

6. A process challenge device comprising:
a chamber formed by a first barrier film; and
a biological indicator stored on a carrier substrate, said carrier substrate enclosed within said chamber formed by said first barrier film;
wherein the combination of said biological indicator, said carrier substrate, and said first barrier film are tailored for use in a particular sterilization, biological inactivation, or disinfection process used on a particular product and package combination,
and wherein said first barrier film is multilayered.

7. A process challenge device comprising:
a chamber formed by a first barrier film;
a biological indicator stored on a carrier substrate, said carrier substrate enclosed within said chamber formed by said first barrier film;
a second chamber;
and a separation means between said first chamber and said second chamber;
wherein the combination of said biological indicator, said carrier substrate, and said first barrier film are tailored for use in a particular sterilization, biological inactivation, or disinfection process used on a particular product and package combination.

8. The process challenge device of claim 7, wherein said second chamber encloses a quantity of a culture medium.

9. The process challenge device of claim 8, wherein said culture media is a soybean casine digest medium.

10. The process challenge device of claim 7 further comprising a means for indicating that the device has been exposed to a sterilization, biological inactivation, or disinfection process.

11. The process challenge device of claim 7, wherein said second chamber is formed from a second barrier film, said second barrier film being formed from a material different than said first barrier film.

12. The process challenge device of claim 11, wherein said second barrier film of said second chamber provides a different resistance to a particular sterilization, biological inactivation, or disinfection process than said first barrier film of said first chamber.

13. A process challenge device comprising:
   a first chamber and a second chamber, said first chamber being formed by a first film, said second chamber being formed by a second film;
   a biological indicator organism residing on a carrier substrate, said carrier substrate being enclosed within said first chamber;
   a quantity of a culture medium enclosed within said second chamber; and
   a separation means between said first and second chambers.

14. The process challenge device of claim 13, wherein the combination of said indicator organism, said carrier substrate, and said barrier film materials are tailored for use in a particular sterilization, biological inactivation, or disinfection process used on a particular product and package combination.

15. The process challenge device of claim 13, wherein said separation means between said first and second chambers is frangible.

16. The process challenge device of claim 13, wherein said separation means between said first and second chambers is removable.

17. The process challenge device of claim 13, wherein said separation means between said first and second chambers is breachable.

18. The process challenge device of claim 13 wherein said first film of said first chamber is formed from a material with properties different than a material forming said second film of said second chamber.

19. The process challenge device of claim 13 wherein said first film provides a different resistance to a sterilization, biological inactivation, or disinfection process than a resistance provided by said second film to said sterilization, biological inactivation, or disinfection process.

20. The process challenge device of claim 13 further comprising means for indicating that the device has been exposed to a sterilization, biological inactivation, or disinfection process.

21. A method of using a process challenge device comprising the following steps:
   (a) placing, into a device for sterilization, biological inactivation, or disinfection, a process challenge device having a chamber formed by a film, a biological indicator stored on a carrier substrate, said carrier substrate enclosed within said chamber formed by said film, said biological indicator, said carrier substrate, and said barrier film being tailored for use in a particular sterilization, biological inactivation, or disinfection process used on a particular product and package combination;
   (b) exposing said process challenge device and a product package combination to the sterilization, biological inactivation, or disinfection process conditions;
   (c) removing said process challenge device from proximity to said product package combination after the process is completed;
   (d) removing said carrier substrate containing said biological indicator from said process challenge device in an aseptic manner;
   (e) culturing said carrier substrate of step (d) to determine possible growth of said indicator organism.

22. A method of using a process challenge device comprising the following steps:
   (a) placing, into a device for sterilization, biological inactivation, or disinfection, a process challenge device having a first chamber and a second chamber formed by one or more films, and a separation means between said first and second chambers, said first chamber enclosing a carrier substrate, said substrate including a biological indicator organism thereon, said second chamber enclosing a quantity of a culture medium, said biological indicator, said carrier substrate, and said barrier film being tailored for use in a particular sterilization, biological inactivation, or disinfection process used on a particular product and package combination;
   (b) exposing said process challenge device and a product package combination to the sterilization, biological inactivation, or disinfection process conditions;
   (c) removing said process challenge device from proximity to said product package combination after the process is completed;
   (d) opening said barrier between said first and second chamber;
   (e) causing said culture medium to contact said indicator organisms;
   (f) incubating said indicator organisms to determine possible growth of said indicator organism.

* * * * *